United States Patent [19]

Weintraub et al.

[11] 4,013,785
[45] Mar. 22, 1977

[54] APAP TABLET CONTAINING FUMED SILICA AND PROCESS FOR MANUFACTURING SAME

[75] Inventors: Leonard Weintraub, Millburn; Allan H. Rosenberg, Randolph, both of N.J.

[73] Assignee: Bristol-Myers Company, New York, N.Y.

[22] Filed: Mar. 21, 1975

[21] Appl. No.: 560,913

[52] U.S. Cl. .............................. 424/23; 424/324; 424/357
[51] Int. Cl.$^2$ ........................................ A61K 47/00
[58] Field of Search .................... 424/23, 357, 324

[56] References Cited

UNITED STATES PATENTS

| | | | |
|---|---|---|---|
| 2,038,694 | 4/1936 | Wiggins | 424/23 |
| 2,951,791 | 9/1960 | Stearns | 424/357 X |
| 3,101,299 | 8/1963 | Ferrand | 424/230 |
| 3,148,124 | 9/1964 | Gaunt | 424/22 |
| 3,173,835 | 3/1965 | Weiner et al. | 424/357 X |
| 3,400,197 | 9/1968 | Lippmann | 424/21 |
| 3,923,969 | 12/1975 | Baukal et al. | 424/19 |
| 3,946,110 | 3/1976 | Hill | 424/230 |

FOREIGN PATENTS OR APPLICATIONS

| | | |
|---|---|---|
| 2,005,410 | 9/1970 | Germany |
| 2,163,035 | 6/1973 | Germany |

OTHER PUBLICATIONS

Cabot Corp. Brochure "Cab-O-Sil Properties and Functions" 35 pages.
Kirk-Othmer Encyclopedia of Chemical Technology vol. 12 (1954) pp. 345, 358, 359, 360, entry "Silica Gel–Materials Related to Silica Gel.".
Siffert et al. Bull. Soc. Chem. Fr. 1970 (8–9):28-33–2839 "Surface Organic Derivatives of Silica; Reaction of Aerosil with Various Phenols".
Merck Index 8th Ed. (1968) p. 5 entry–Acetaminophen "APAP".
Monkhouse et al. J. Pharm. Sci. 61(9):1430–1441 Sept. 1972 "Use of Adsorbents in Enhancement of Drug Dissolution I–II".

*Primary Examiner*—Shep K. Rose
*Attorney, Agent, or Firm*—Irving Holtzman; George A. Mentis; David J. Mugford

[57] ABSTRACT

Preparation of APAP tablet containing fumed silica by (a) forming a solution of APAP in an organic solvent, (b) suspending or dispersing in said solution powdered fumed silica, (c) drying said suspension to form a APAP-fumed silica mix, and (d) pressing a mixture containing said APAP-fumed silica mix into a tablet.

13 Claims, No Drawings

APAP TABLET CONTAINING FUMED SILICA AND PROCESS FOR MANUFACTURING SAME

This invention relates to analgesic tablets containing n-acetyl-p-aminophenol (hereinafter referred to as APAP). More particularly, it concerns tablets of this character which have relatively high absorption rates for APAP as measured by the blood plasma level of APAP over time after ingestion of APAP.

APAP has long been known in the pharmaceutical arts to be useful as an analgesic and/or antipyretic agent and has found its way into several commercially available products. However, the speed at which its action takes effect and the amount of it which is absorbed is less than desirable and this is at least partly due to the relatively slow rate at which it is absorbed into the blood stream from the gastrointestinal tract.

It has now been found that the absorption rate of APAP from the gastrointestinal tract can be dramatically improved if the APAP is processed by: (1) dissolving it in a solvent; (2) suspending in the solution so formed from about 5.2 to about 25% by weight (based on the weight of the APAP in said solution) of finely powdered fumed silica carrier that is substantially insoluble in said solution; and (3) then drying this suspension preferably by evaporating it to dryness. This dried product hereinafter referred to as "dried APAP mix" will contain from about 5 to about 20% by weight of the fumed silicon dioxide based on the total weight of the "dried APAP mix," the balance being made up substantially of APAP.

The fumed silicon dioxides that are useful for the purposes of the present invention are exemplified by commercial products sold under the trade name CAB-O-SIL. These are available in a variety of grades as described in more detail below; good results being obtained with materials having varying particle sizes and surface areas.

In the preferred practice of the present invention, the "dried APAP mix" is first prepared using the aforesaid evaporation process. The solid material resulting from this evaporation step is then ground and sifted through a 12 to 400 mesh screen; the preferred range being between 60 to 100 mesh. The resulting particulate "dried APAP mix" may be employed as such. However, from a practical point of view, it is more useful when put up in tablet form. This may be accomplished by using standard tabletting techniques well known to those skilled in the art.

In preparing tablets containing the present "dried APAP mix", there may be incorporated in this mix prior to tabletting the conventional tabletting aids or ingredients. Typical among these materials there may be mentioned: binders, disintegrants, lubricants, diluents, colors, etc. These are more specifically exemplified by the following:

*binders:* microcrystalline cellulose, lactose, sucrose;
*disintegrants:* corn starch, potato starch, sodium starch glycolate;
*lubricants:* magnesium stearate, talc, stearic acid;
*diluents:* lactose, sucrose.

It may sometimes be advantageous to also incorporate in these tablets other pharmaceutically active ingredients. By way of illustrating these other pharmaceutically active materials, the following may be mentioned: analgesics such as aspirin, propoxyphene; decongestants such as phenylpropanolamine (or the hydrochloride), phenylephrine (or the hydrochloride); antihistamines such as methapyriline (or its hydrochloride), diphenhydramine (BENADRYL), chlorpheniramine; antacids such as calcium carbonate, magnesium hydroxide, aluminum hydroxide. However, in the preferred embodiments of this invention, the pharmaceutically active material will consist essentially of APAP.

As mentioned above, any of a variety of fumed silicon dioxides well known to those skilled in this art are suitable for the present purposes. Although they may vary considerably in particle size, they will ordinarily be of a particle size falling in the range of from 0.007 to 0.050 microns.

The fumed silicon dioxides, commercially available under the trade name CAB-O-SIL, are sold in several grades that are identified as CAB-O-SIL EH—5, —H—5; —HS—5; —L—5; —M—5; —MS—5, —M—7; —MS—7 and —M—7D. These are products of the Cabot Corporation and are made by a vapor phase reaction process. They are produced by the hydrolysis of silicon tetrachloride at 1100° C. This process produces a colloidal silica. Since they are produced at a high flame temperature, they are generally referred to as "fumed" silicas. The basic chemical reaction is as follows:

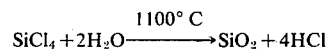
$$SiCl_4 + 2H_2O \xrightarrow{1100°\,C} SiO_2 + 4HCl$$

All grades of CAB-O-SIL have certain properties in common. These are given in Table I below:

TABLE I

| | |
|---|---|
| Bulking value, gallons per 100 lbs, | 5.5 |
| 325 Mesh residue - max. | 0.02% |
| Silica content | 99.8 |
| Specific gravity | 2.2 |
| Refractive index | 1.46 |
| Color | White |
| X-Ray structure | Amorphous |

Different grades of CAB-O-SIL also vary in certain properties. Table II below illustrates this.

TABLE II

| CAB-O-SIL properties | CAB-O-SIL Grades | | | | | | | | |
|---|---|---|---|---|---|---|---|---|---|
| | EH-5 | H-5 | HS-5 | L-5 | M-5 | MS-5 | M-7 | MS-7 | M-7D |
| Surface area m²/gm (BET) | 390±40 | 325±25 | 325±25 | 50 | 200±25 | 200±25 | 200±25 | 200±25 | 200±25 |
| Particle size micron | 0.007 | 0.007 | 0.007 | 0.050 | 0.012 | 0.012 | 0.012 | 0.012 | 0.012 |
| Density lbs./cu. ft. | 2.3 max. | 2.3 max. | 2.3 max. | 7 | 2.3 max. | 2.3 max. | 4.0±0.2 | 4.0–5.0 | 6.0 min. |
| Ignition loss (1000° C. moisture-free basis) | 2.5% | 2% | 2% | 0.5% | 1% | 1% | 1% | 1% | 1% |
| pH (4% aqueous dispersion) | 3.5–4.2 | 3.5–4.2 | 3.6–4.1 | 4.0 | 3.5–4.2 | 3.6–4.1 | 3.5–4.2 | 3.6–4.2 | 3.5–4.2 |

Although any of the fumed silicon dioxides mentioned above are useful for the present invention, the preferred materials are CAB-O-SIL EH—5 and CAB-O-SIL M—5, the optimum results being obtained with CAB-O-SIL M—5.

As also pointed out above, in the process of the present invention, a solution of APAP is first preferably formed in an organic solvent and the powdered fumed silicon dioxide is suspended or dispersed in the solution so formed. Any suitable organic solvent may be employed for this purpose so long as it meets two criteria: (1) the APAP must be sufficiently soluble in it at the temperature at which the evaporation is carried out (e.g., at least 1%) and (2) the powdered fumed silicon dioxide must be sufficiently insoluble in it (e.g., not more than 1/2%). A number of solvents are known that meet these criteria. Among these, mention may be made of methyl alcohol, ethyl alcohol, isopropanol, acetone ethyl acetate, etc.

The APAP solutions used in practicing the process of the present invention can vary somewhat with regard to the APAP concentration. Ordinarily, this will be in the range of from 1 to 30% and preferably 5 to 30% by weight of APAP based on the total weight of APAP-organic solvent solution. For reasons of economy, it is preferable to use the most concentrated solutions of APAP attainable.

Several techniques are available in the prior art for drying the suspension or dispersion of the fumed silicon dioxide in APAP solution in accordance with the present invention. These include such procedures as spray drying, oven drying, vacuum drying with or without heat or evaporation, the latter being the preferred procedure. In one evaporation procedure, the suspension is warmed slightly (e.g., 22° to 28° C) and stirred for an extended period of time (e.g., 2 to 10 hours) under a stream of warm air until most of the solvent is evaporated. The evaporation can then be completed under vacuum drying at somewhat elevated temperature (e.g., 50° to 70° C) until the product is dried (e.g., 4 to 6 hours).

An equally effective method for evaporating the dispersion of fumed silicon dioide in APAP solution is to evaporate from hot solution. The dispersion of silicon dioxide in APAP solution is stirred in a jacketted kettle in which hot water or steam can be circulated through the jacket. The solvent can be heated to any temperature up to its boiling point. This permits the economical processing of the greatest amount of APAP in the least solvent. In addition, the processing time is reduced considerably as compared to the process where the evaporation of solvent is conducted at about room temperature.

As mentioned above, the dried APAP mix is then lightly ground. However, in some instances the grinding step may be dispensed with as, for example, when a spray drying technique is employed in drying the APAP-fumed silica suspension or dispersion. Several procedures that may be used to accomplish the grinding are described below:

1. Mortar and Pestle

The dried APAP powder mix is ground in a stone mortar. The ground sample is then screened and the various particle size fractions collected can be used for tabletting.

2. Ball Mill

The dried APAP powder mix is placed in a stone ball mill. The mill is automatically rotated on a moving belt until the desired particle size is obtained. The ground sample is screened and separated into various particle size fractions as above.

3. Grinding through Wire Screen

The dried APAP powder mix is ground by forcing the mix through a wire screen. The ground material is now ready for tabletting.

4. Air Attrition Milling.

The particulate dried APAP mix resulting from the last grinding step is now ready for tabletting. As previously noted, any of the conventional tabletting procedures known in the prior art may be used in the present invention. In preferred forms of the invention, the following tabletting procedures are employed:

1. Manually Compressed Tablets

The dried APAP mix consisting of APAP and CAB-O-SIL is blended with microcrystalline cellulose and corn starch. This blend is compressed into tablets by placing a pre-weighed amount of blend in the dye of a Manesty F single punch press and manually compressing the powder using a 7/16 inch SC punch. Tablet thickness varies between 0.220 to 0.230 inches. Tablet weights are periodically checked to insure proper tablet thickness and hardness.

2. Power Run Tablets

The dried APAP mix consisting of APAP and CAB-O-SIL is blended with microcrystalline cellulose, sodium starch glycolate and stearic acid. This blend is compressed into tablets using the Manesty F single punch press operating in the power mode. A 7/16 inch SC punch is employed. Tablet weights are periodically checked to insure proper tablet content as well as thickness and hardness.

Tablets prepared in accordance with the present invention may vary with respect to the APAP content. This will depend upon the size of the tablet, the size of the dose to be administered at any one time and the number of tablets to be given at any time. As used herein, the term unit dosage amount is used to describe the quantity of material in question that goes into a single tablet. This may comprise all or a portion of the dose of material to be administered at any one particular time. Ordinarily, the unit dosage amount of APAP contained in the tablets of the present invention will vary from about 150 milligrams to about 650 milligrams and will preferably amount to about 324 or 325 milligrams of APAP. The fumed silicon dioxide in each tablet will comprise about 5% to 20% by weight based on the total weight of APAP-fumed silicon dioxide mix.

It has been suggested in the prior art that the dissolution rates of certain drugs may be increased by depositing the drug in "miniscular form" on the surface of an absorbant. In this connection, attention is invited to two articles by Monkhouse and Lach entitled "Use of Absorbants in Enhancement of Drug Dissolution" I and II appearing in the Journal of Pharmaceutical Science, Vol. 61, No. 9, September 1972, pages 1430–1441. These references are concerned with increasing the dissolution rate of relatively insoluble drugs. More particularly, the drugs mentioned are indomethacin, aspirin, hydrochlorothiazide, chloramphenicol, sulfaethidole, reserpine, guiseofulvin, probucol and oxolinic acid. However, no mention is made in this reference of the use of APAP. Furthermore, APAP differs from the drugs mentioned in these references in that it is not as highly insoluble in water as are the latter.

The differences between the drugs disclosed by Monkhouse and Lach, on the one hand, and APAP, on the other hand, are further demonstrated by the difference in behavior that they exhibit when different fumed silicas are employed. Monkhouse and Lach maintain that with the drugs that they were testing the surface area of the absorbant is the controlling factor in the dissolution rate of the product; the rate increasing with the increase in surface area. Thus, in the case of indomethacin, they show that with fumed silicon dioxide EH 5, which has a surface area of $390 \pm 40$ m.$^2$/g, the dissolution rate is faster than with fumed silicon dioxide M-7 which has a surface area of $200 \pm 25$ m.$^2$/g. Applicants have found that, on the contrary, in the case of APAP, a faster dissolution rate is obtained with the smaller surface area fumed silicon dioxide. Applicants have compared dissolution rate of APAP compositions prepared in accordance with the evaporation process using fumed silicon dioxide EH 5 and fumed silicon dioxide M-5, which is similar in surface area to fumed silicon dioxide M-7 and obtained better results with the smaller surface area material.

To illustrate this, the dissolution rate of tablets which differed only on the fact that they contained CAB-O-SIL M-5 or CAB-O-SIL EH-5 was measured by dropping two tablets of each kind into 350 ml. of modified gastric solution (0.01 N HCl solution) contained in a jacketted beaker. This solution is stirred at 50 rpm by a propeller stirrer and the temperature of the solution is maintained at 38° C. The times for dissolution of different percentages of the APAP are given in Table III below; $t_{25}$, $t_{50}$, and $t_{75}$ being the times for 25, 50 and 75% respectively of the APAP contained in the tablets to dissolve.

TABLE III

| % CAB-O-SIL in Tabl. | CAB-O-SIL S.A. m$^2$/gm | $t_{25}$(min.) | $t_{50}$(min.) | $t_{75}$(min.) |
|---|---|---|---|---|
| 5% M-5 | $200 \pm 25$ | .8 | 1.4 | 2.2 |
| 5% EH-5 | $390 \pm 40$ | .9 | 1.7 | 4.4 |

In addition, the Monkhouse and Lach dissolution rate studies are concerned with powder materials and not tablets with which the present invention is concerned. There is often a great deal of difference between the rate at which drugs dissolve when put up in powder form as compared with the corresponding tablets.

Furthermore, Monkhouse and Lach maintain that the products they obtain are such that the drug is deposited in miniscular form on the surface of the absorbant. Applicants have found that with regard to APAP CAB-O-SIL particles, which are the smaller particles, are in fact deposited on the larger particles of APAP.

Although Monkhouse and Lach go into great detail with regard to the dissolution rates of their preparations, they are totally silent as to the absorption rate of their products from the gatrointestinal tract into the blood stream. Dissolution rate studies have sometimes been used as screening tests for preparations in searching for products that have adequate absorption rates from the gastrointestinal tract. However, the fact that preparations may have comparable in vitro dissolution rates is no indication that they will have comparable in vivo absorption rates.

Applicants have verified this specifically with various APAP-fumed silicon dioxide preparations with which the present invention is concerned. Thus, it has been found that APAP-fumed silicon dioxide tablets containing 2½% by weight of the fumed silicon dioxide based on the total weight of the dried APAP mix have a dissolution rate which is not significantly different from a tablet that is the same in all respects, excepting that it contains 10% by weight of the fumed silicon dioxide based on the total weight of the dried APAP mix. However, notwithstanding the fact that the dissolution rates of the respective materials are not significantly different, the 10, 20 and 40 minute post ingestion plasma APAP levels of the 10% CAB-O-SIL M-5 product were significantly higher (2–3 times higher) than a conventional APAP tablet while the plasma APAP levels of the 2½% CAB-O-SIL M-5 tablet were not different than the same lot of the same conventional APAP tablet at the same times post ingestion. In addition, the peak APAP level was attained about 25 minutes post ingestion with the 10% CAB-O-SIL tablet, whereas, it was attained 50 minutes after ingestion of the conventional APAP tablet and the 2½% CAB-O-SIL tablet. The blood level and dissolution data are summarized in Table IV below. Plasma APAP levels were determined for 20 subjects in a two way crossover study in which each subject received either the conventional APAP tablet or the 10% CAB-O-SIL tablet one week and the following week received the other tablet. In a second study another 20 subject panel received the conventional APAP tablet and the 2½% CAB-O-SIL tablet. In this way the absorption of two different tablets by each subject in a study is compared. Plasma levels cannot be compared between studies but comparative performance of two products towards a third product can be measured.

TABLE IV

| Tablet | Avg. Free APAP Plasma Levels (mcg/ml) Time after gestion | | | Dissolution Rate at 38° C | | |
|---|---|---|---|---|---|---|
| | 10 min. | 20 min. | 40 min. | $t_{25}$(min.) | $t_{50}$(min.) | $t_{75}$(min.) |
| Study 1 | | | | | | |
| *10% CAB-O-SIL | 3.70 | 7.65 | 6.50 | 0.6 | 1.1 | 1.7 |
| ***Conventional APAP tablet | 1.14 | 4.27 | 4.95 | 2.5 | 3.9 | 7.6 |
| Study 2 | | | | | | |
| **2½% CAB-O-SIL | 2.9 | 6.8 | 7.1 | 0.6 | 1.0 | 1.8 |
| ***Conventional APAP tablet | 2.1 | 5.0 | 7.3 | 2.5 | 3.9 | 7.6 |

*10% CAB-O-SIL tablet is that described in Example 1B. All tablets contain 324 mg. APAP
**2 ½% CAB-O-SIL tablet is that described in Example 5B All tablets contain 324 mg. APAP
***Conventional tablet is commercial APAP tablet containing disintegrants, binders and APAP (324 mg.) but no CAB-O-SIL the reverse is true. Photomicrographic examination of the products of the present invention shows that the The use of fumed silica as a glidant in a pharmaceutical preparation is known in the prior art. In this connection, see U.S. Pat. No. 3,173,835. However, this reference nowhere teaches the evaporation processing of APAP which is characteristic of the present invention nor the increase in APAP absorption rate that accompanies this process. It has also been suggested that sustained release tablets might also be prepared using a CAB-O-SIL in conjunction with a lipid material as a matrix for the pharmaceutically active material. APAP is among the active materials that can be employed in preparing these tablets. (See U.S. Pat. No. 3,400,197). However, again in this patent there is no teaching of the evaporation processing of APAP taught in the present invention or the beneficial increase in absorption rate of the APAP.

The following Examples are given to further illustrate the present invention. It is understood, however, that the invention is not limited thereto.

EXAMPLE 1

APAP — 10% CAB-O-SIL M-5 Product

A. Four hundred and nine (409 g.) of acetaminophen powder was dissolved in 3000 ml. of methanol at room temperature. Forty-five (45 g.) of CAB-O-SIL M-5 was added, with constant stirring to the solution. The resulting suspension was warmed slightly and stirred for 2 to 10 hours under a stream of warm air until most of the solvent had evaporated. The resulting mixture was then vacuum dried at 60° C for 4 to 6 hours. The product was then ground lightly in a mortar and pestle and was screened to a 100 mesh to 200 mesh fraction.

B. The powder obtained from this process, i.e., dried APAP mix was used to prepare tablets. Seventy-two (72 g.) of the dried APAP mix was blended with 23 g. of microcrystalline cellulose and 5 g. of corn starch. Five hundred (500) mg. portions of the blend are placed in the dye of a Manesty F single punch press and then manually compressed into tablets using a 7/16 inch SC punch. Tablet weights are periodically checked to insure proper thickness and hardness. Thickness varies between 0.220 to 0.230 inch. Tablets consist of 324 mg. APAP, 36 mg. CAB-O-SIL M-5, 115 mg. microcrystalline cellulose and 25 mg. corn starch.

EXAMPLE 2

APAP — 5% CAB-O-SIL M-5 Product

A. The procedure given in Example 1 section A above was followed excepting that 431 g. of APAP and 23 g. of CAB-O-SIL M-5 was employed. The powder resulting from this procedure was tabletted using the procedure of Section B below.

B. The procedure is the same as for Example 1B except that the blend consists of 68.2 g. dried APAP mix, 23.0 g. microcrystalline cellulose and 5.0 g. corn starch. Tablets consist of 324 mg. APAP, 17 mg. CAB-O-SIL M-5, 115 mg. microcrystalline cellulose and 25 mg. corn starch.

EXAMPLE 3

APAP — 5% CAB-O-SIL EH-5 Product

A. The procedure of Example 2 above was followed excepting that 23 g. of CAB-O-SIL EH-5 was used. The powder obtained from the above procedure was tabletted using the process set out in Example 2B above.

EXAMPLE 4

APAP — 5% CAB-O-SIL M-5 Product

A. Eight hundred sixty two (862 g.) of APAP powder was dissolved in 2500 ml. of methanol at 41° C. Forty-five (45 g.) of CAB-O-SIL M-5 was added, with constant stirring to the solution using a Hobart mixer. The resulting suspension was kept at 41° C for 20 to 40 minutes until most of the solvent had evaporated. The resulting mixture was then vacuum dried at 60° C for 4 to 6 hours. The product was lightly ground through a 60 mesh wire screen.

B. The powder obtained from this process was used to prepare tablets. One hundred two and three tenths (102.3) g. of the dried APAP mix was blended with 47.7 g. of microcrystalline cellulose, 7.5 g. of sodium starch glycolate and 1.5 g. of stearic acid. This blend was fed into a Manesty F single punch press operating in the power mode and compressed into tablets using a 7/16 inch SC punch. Tablet weights were periodically checked to insure proper tablet content, thickness and hardness. Tablets consist of 324 mg. APAP, 17 mg. CAB-O-SIL M-5, 159 mg. microcrystalline cellulose, 25 mg. sodium starch glycolate and 5 mg. stearic acid.

EXAMPLE 5

APAP — 2½% CAB-O-SIL M-5 Product

A. The procedure of Example 1 section A was followed excepting that 443 g. of APAP and 11.5 g. of CAB-O-SIL M-5 was employed. The powder resulting from the above procedure was tabletted using the process set out in section B below.

B. The procedure is the same as used for Example 1B except that the blend consisted of 66.4 g. dried APAP mix, 23.0 g. microcrystalline cellulose and 5.0 g. corn starch. Tablets consist of 324 mg. APAP, 8 mg. CAB-O-SIL M-5, 115 mg. microcrystalline cellulose and 25 mg. corn starch.

What is claimed is:

1. A process for preparing a tablet containing n-acetyl-p-aminophenol in therapeutically effective quantities which comprises:
    a. forming a solution of n-acetyl-p-aminophenol in an organic solvent containing from about 1 to 30% by weight of n-acetyl-p-aminophenol based on the total weight of said solution;
    b. distributing in said solution from about 5.2% to 25% by weight based on the weight of n-acetyl-p-aminophenol of powdered fumed silicon dioxide to form a dispersion or suspension of said powdered fumed silicon dioxide is said solution;
    c. drying said dispersion or suspension to form a dried mix comprising n-acetyl-p-aminophenol and fumed silicon dioxide; and
    d. pressing a quantity of tabletting mix containing said dried particulate mix comprising a unit dosage amount of n-acetyl-p-aminophenol and fumed silicon dioxide to form a tablet;
    said organic solvent being selected so that said n-acetyl-p-aminophenol is soluble therein and said fumed silicon dioxide is substantially insoluble therein; the relative amounts of said n-acetyl-p-aminophenol and said fumed silicon dioxide employed being such that said dried mix contains from about 5 to 20% by weight of said fumed silicon dioxide based on the combined weight of n-acetyl-p-aminophenol and fumed silicon dioxide.

2. A process according to claim 1 wherein said drying is accomplished by evaporating said dispersion or suspension.

3. A process according to claim 2 in which the evaporation-dried mix of n-acetyl-p-aminophenol is ground to particulate form.

4. A process according to claim 2 wherein said unit dosage amount of n-acetyl-p-aminophenol is in the range of from about 150 milligrams to about 650 milligrams.

5. A process according to claim 2 wherein said solvent is selected from the group consisting of methyl alcohol, ethyl alcohol, isopropanol, acetone and ethyl acetate.

6. A process according to claim 2 wherein the fumed silicon dioxide has a particle size in the range of from about 0.007 to 0.05 microns.

7. A process according to claim 6 wherein said dried mix of n-acetyl-p-aminophenol is ground to a mesh size of from about 12 to about 400 to produce said particulate dry mix of n-acetyl-p-aminophenol and fumed silicon dioxide.

8. A process according to claim 6 wherein said dried mix of n-acetyl-p-aminophenol is ground to a mesh size of from about 60 to about 100 mesh.

9. A process according to claim 1 in which said dry particulate mix of n-acetyl-p-aminophenol and fumed silicon dioxide is mixed with a binder.

10. A process according to claim 9 in which said tabletting mix also includes a disintegrant.

11. A process according to claim 10 in which said tabletting mix also includes a lubricant.

12. As a unit dosage form a tablet made by the process of claim 1.

13. As an article of manufacture, a tablet comprising from about 150 to 650 milligrams of n-acetyl-p-aminophenol and fumed silicon dioxide, said fumed silicon dioxide being present in an amount of from about 5 to 20% by weight based on the combined weight of n-acetyl-p-aminophenol and fumed silicon dioxide.

* * * * *

Disclaimer 4,013,785.—*Leonard Weintraub*, Millburn, and *Allan H. Rosenberg*, Randolph, N.J. APAP TABLET CONTAINING FUMED SILICA AND PROCESS FOR MANUFACTURING SAME. Patent dated Mar. 22, 1977. Disclaimer filed Dec. 8, 1977, by the assignee, *Bristol-Myers Company*.

Hereby enters this disclaimer to claims 10 and 13 of said patent.

[*Official Gazette September 12, 1978.*]